United States Patent [19]

Hamel et al.

[11] 4,237,160

[45] Dec. 2, 1980

[54] 3-HYDROXYMETHYLDIBENZO[B,F]THIE-PINS AS PROSTAGLANDIN ANTAGONISTS

[75] Inventors: Pierre A. Hamel, Laval; Joshua Rokach, Chomedey-Laval, both of Canada

[73] Assignee: Merck Sharp & Dohme (I.A.) Corp., Rahway, N.J.

[21] Appl. No.: 97,755

[22] Filed: Nov. 27, 1979

[51] Int. Cl.$^3$ ..................... A61K 31/38; C07D 337/14
[52] U.S. Cl. ....................... 424/275; 549/12; 260/465 G; 260/465 E; 260/465 F; 562/426; 562/432
[58] Field of Search .......................... 549/12; 424/275

[56] References Cited

U.S. PATENT DOCUMENTS

| 3,509,154 | 4/1970 | Fouche et al. | 544/12 X |
| 3,905,989 | 9/1975 | Hodson et al. | 544/12 X |
| 4,025,635 | 5/1977 | Hodson et al. | 424/269 |

OTHER PUBLICATIONS

Nogradi et al., J. Chem. Soc. Chemical Communications, Section D 1970, pp. 158 to 160 (note 1 e) (cited by Examiner).
Derwent Abstract No. 8369Y/05, Abst. of Nippon Chemifar, British Application 046099 published Dec. 16, 1976.
Derwent Abstract No. 94674X/51, Abst. of Nippon Chemifar, published Japanese Application 129,490 (12/9/76).
Derwent Abstract No. 56636X/30, abst. of Nippon Chemifar, published Japanese Application 139961 (6/7/76).
Chemical Abstracts, vol. 73, abst. no. 109723 (1970) (abst. of Jilek et al.).
Chemicals Abstracts, vol. 84, abst. no. 17276 (1976) (abst. of Sindelar et al.).
Chemical Abstracts, vol. 82, abst. 156214b (1975) (cited by Examiner) (abst. of Sindelar et al.).
Current Abstracts of Chemistry, vol. 66, issue 718, abst. 260474 (1977) (abst. of Sindelar et al.).
Pelz et al., Collection Czechoslov. Chem. Commun. vol. 34, pp. 3936 to 3943 (1969).

*Primary Examiner*—John D. Randolph
*Attorney, Agent, or Firm*—Thomas E. Arther; Mario A. Monaco; Rudolph J. Anderson, Jr.

[57] ABSTRACT

Novel 3-hydroxymethyldibenzo[b,f]thiepin and derivatives are prepared and employed in the treatment and control of allergic conditions such as allergic asthma.

22 Claims, No Drawings

3-HYDROXYMETHYLDIBENZO[B,F]THIEPINS AS PROSTAGLANDIN ANTAGONISTS

SUMMARY OF THE INVENTION

This invention relates to prostaglandin antagonists useful in treating a variety of conditions, such as allergic asthma where excessive contractile activity of prostaglandins and prostaglandin biosynthetic intermediates occur. These prostaglandin antagonists are 3-hydroxymethyldibenzo[b,f]thiepins having the structural formula:

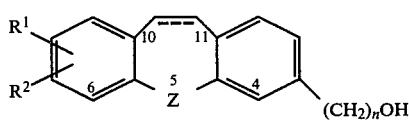

wherein
n is an integer from 1 to 4;
Z is thio, sulfinyl, or sulfonyl;
$R^1$ and/or $R^2$ is hydrogen, halogen including chloro, bromo, fluoro and iodo, amino, $C_1$ to $C_4$ alkyl, $C_1$ to $C_4$ alkanoyl, hydroxyl, $C_1$ to $C_4$ alkoxy, thiol, $C_1$ to $C_4$ alkylthio, $C_1$ to $C_4$ alkylsulfinyl, $C_1$ to $C_4$ alkylsulfonyl, trifluoromethyl, trifluoromethylthio, cyano, nitro, and $C_1$ to $C_4$ alkyl or dialkylamino, aralkyl including benzyl and phenethyl, hydroxyalkyl as $CH_3CHOH$; and
the dotted line indicates either an olefinic bond or saturation at the 10-, 11-position.

As used herein, the term halogen (or halo) includes chlorine, bromine, iodine, and fluorine. Unless otherwise specifically stated, the terms loweralkyl and loweralkoxy include straight and branched chain alkyl and alkoxy groups having 1 to 4 carbon atoms in the alkyl or alkoxy moiety such as, for example, methyl, ethyl, n-propyl, isopropyl, n-butyl, methoxy, ethoxy, n-propoxy, and isobutoxy. The term loweralkanoyl includes straight or branched chain alkanoyl groups having 1 to 4 carbon atoms in the alkanoyl moiety such as, for example, formyl, acetyl, propanoyl, and isobutyryl. The terms aralkyl includes straight or branched chain alkyl radicals having one of the hydrogens replaced by a phenyl or substituted phenyl group including phenyl, halophenyl such as chloro, bromo, iodo, and fluorophenyl, nitrophenyl, aminophenyl, hydroxyphenyl, loweralkylphenyl, and the like.

These dibenzo[b,f]thiepin derivatives antagonize the actions of contractile prostaglandins, such as $PGF_{2\alpha}$, $PGG_2$, $PGH_2$, and $TXA_2$. The use of agents which act as prostaglandin antagonists offers new approaches to therapy in a number of disease states. For example, certain prostaglandins, such as $PGF_{2\alpha}$, PGG, and $PGH_2$, are potent contractants of bronchial muscle. Indeed human asthmatics have been shown to be especially sensitive to the bronchial constricting action of $PGF_{2\alpha}$.

In addition to the involvement of contractile prostaglandins in chronic obstructive lung disease (or asthma), prostaglandins are known to play a role in other allergic conditions, as well as inflammation, diarrhea, hypertension, angina, platelet aggregation, cerebral spasm, premature abortion, and dismenorrhea.

In addition to the prostaglandin antagonist actions, the dibenzo[b,f]thiepins of this invention are antagonists of slow reacting substance of anaphylaxis (SRS-A). This contractile substance is released in the lung tissue in allergic asthma, and antagonism of its actions contributes to alleviation of this disease.

The dibenzo[b,f]thiepins of this invention are prepared according to the following general reaction scheme:

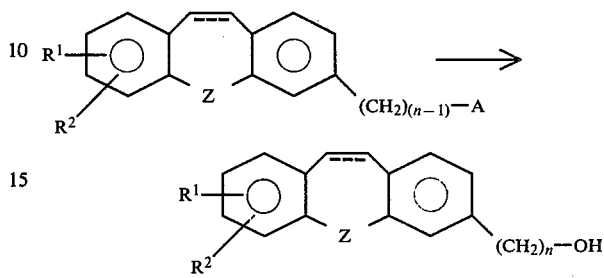

wherein $R^1$, $R^2$, Z, and n are as defined above; and A is COOH or a loweralkyl ester thereof.

As shown in the above reaction scheme, an appropriately substituted dibenzo[b,f]thiepin-3-carboxylic acid of a loweralkyl ester thereof is reduced to the correspondingly substituted 3-hydroxymethyldibenzo[b,f]thiepin by treatment with an alkali metal aluminum hydride, preferably lithium aluminum hydride or borane. Either reagent is effective in reducing a carboxy or a carbalkoxy substituent to the corresponding hydroxymethyl substituent but borane is preferred for the reduction of the carboxyl function in a dibenzothiepin-3-carboxylic acid, 5,5-dioxide. The reduction is conducted in a solvent which is inert under the reaction conditions and may be either a volatile or non-volatile ether. Ethyl ether or other loweralkyl ethers are satisfactory and tetrahydrofuran is a commonly preferred solvent.

The reducing reagent, either lithium aluminum hydride or borane, is employed in a slight excess over the stoichiometric amount needed in order to insure completeness of reaction. The reduction reaction is maintained at a temperature between 0° and 100° C. or the reflux temperature of the solvent. Most acids and esters are reduced relatively completely at room temperature (25° C.) and in a relatively short time (approximately 1 hour), and therefore the reduction is usually conducted by stirring the acid or ester for a period of from 30 minutes to 12 hours at a temperature of from 10° to 40° C. Following the completion of the reaction, the product is isolated by the addition of water and extraction into ether. The ether extract is evaporated to obtain the residual product which is recrystallized from an appropriate solvent.

Products which may be obtained directly by reduction of the appropriate acid are 3-hydroxymethyldibenzo[b,f]thiepin and 3-hydroxymethyldibenzo[b,f]thiepin-5,5-dioxide or derivatives bearing $R_1$ and $R_2$ substituents which are resistant to the reducing effect of lithium aluminum hydride or borane. Ordinarily the 3-hydroxymethyldibenzo[b,f]thiepin 5-oxide or $R_1, R_2$ derivatives thereof are prepared by oxidation of the corresponding 3-hydroxymethyldibenzo[b,f]thiepin with organic peroxides such as peroxy acids like m-chloroperbenzoic acid. The oxidation can be carried further, if an additional equivalent of acid is employed, to produce the corresponding dibenzo[b,f]thiepin-5,5-dioxides. It will be apparent to one skilled in the art that variations in these preparative schemes will allow one to prepare a variety of substituted 3-hydroxymethyldibenzo[b,f]thiepin, as well as the corresponding thiepin-5-oxides and the thiepin-5,5-dioxides.

For example, 8-amino-3-hydroxymethyldibenzo[b,f]thiepin is prepared by reduction of the correspondingly substituted acid or by catalytic hydrogenation of 3-hydroxymethyl-8-nitrodibenzo[b,f]thiepin.

PREPARATION OF STARTING MATERIALS

As described in greater detail in U.S. Application Ser. No. 917,212 filed June 23, 1978, an appropriately substituted mercaptobenzoic acid II ($R^4$=SH) is reacted with m-dibromobenzene III ($R_3$=Br) to obtain the 2-(3-bromophenyl)benzoic acid IV. Or alternatively, an appropriately substituted o-bromobenzoic acid II ($R_4$=Br) is reacted with m-bromobenzenethiol III ($R_3$=SH) to give IV:

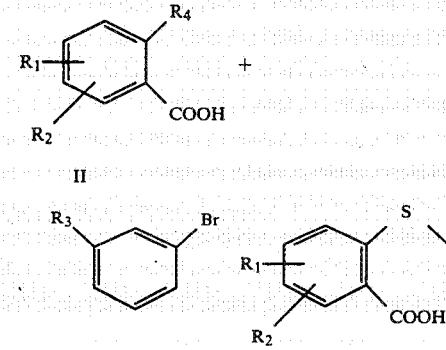

where $R_1$ or $R_2$ are each selected from hydrogen, nitro, amino, $C_1$ to $C_4$ alkanoyl, hydroxyl, $C_1$ to $C_4$ alkoxy, $C_1$ to $C_4$ alkylsulfinyl, $C_1$ to $C_4$ alkylsulfonyl, and $C_1$ to $C_4$ alkyl, trifluoromethyl, and trifluoromethylthio. $R_3$ and $R_4$ are different and alternatively are thiol and bromo.

Generally, the sulfide-forming reaction is carried out according to the methods described by Jilek et al., MONATSH. CHEM. 96, 200 (1965); Protiva et al., Czechoslovakian Patent 121,337, CHEM. ABSTRACTS 68: 105, 247t (1968); and U.S. Pat. No. 3,711,489; and by other procedures well known in the art.

The resulting o-(3-bromophenylthio)benzoic acid (IV) is reduced to the alcohol, brominated, and the bromo replaced with cyano. The cyano derivative is then hydrolyzed to the carboxylic acid V.

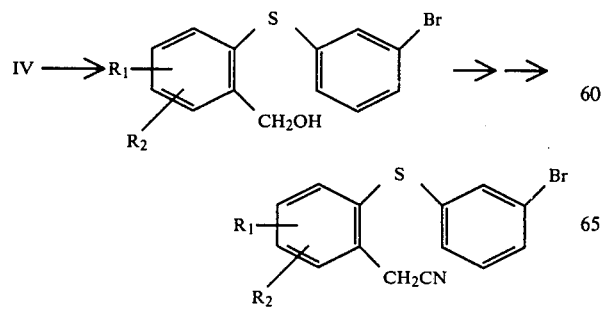

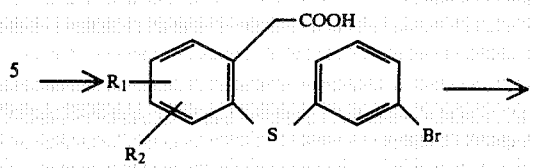

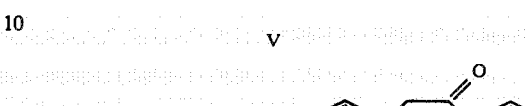

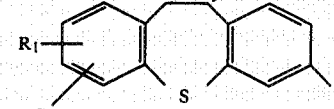

The carboxylic acid V is transformed into the 3-bromo-11-oxo-10,11-dihydrodibenzo[b,f]thiepin by first conversion to the acid halide with thionyl or phosphoryl halide followed by Friedel-Crafts cyclization with a Lewis acid such as aluminum chloride to give VI. Reduction of the ketone VI with alkali metal borohydrides to the alcohol VII, followed by heating in an appropriate solvent such as toluene with catalytic amounts of a mineral acid, such as sulfuric acid or toluenesulfonic acid provides the 3-bromodibenzo[b,f]thiepin VIII.

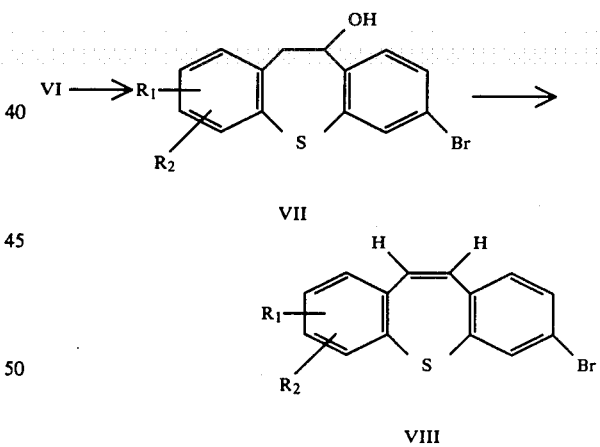

The 3-bromo derivative VIII is then converted to the 3-nitrile IX by reaction with cuprous cyanide in a high boiling polar solvent such as dimethylformamide, N-methylpyrrolidone, and the like.

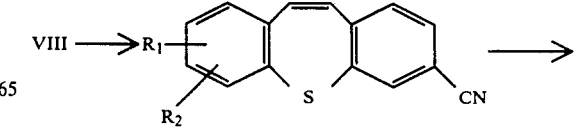

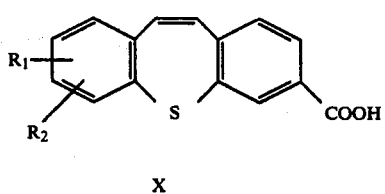

X

The 3-cyano derivative IX may be hydrolyzed with aqueous mineral acid or base to give the dibenzo[b,f]-thiepin-3-carboxylic acid X. Alternatively, the cyano intermediate IX may be oxidized with organic peroxides such as peroxy acids, for example, m-chloroperbenzoic acid and the like, in a stepwise fashion to the corresponding sulfoxide XI and sulfone XII, controlling the molar ratio of oxidant to reductant. This determines the oxidation level of the sulfur. For example, a 1:1 molar ratio results largely in the production of sulfoxide XI. In contrast, a 2:3 molar excess of oxidant results in a yield predominantly comprising the sulfone XII.

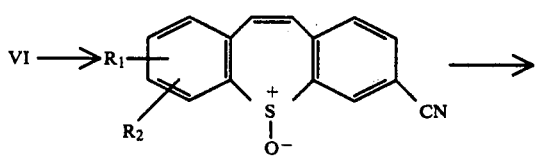

XI

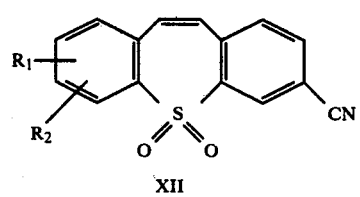

XII

Hydrolysis of XI and XII using aqueous mineral acid or alkali provides the corresponding carboxylic acid XIII and XIV.

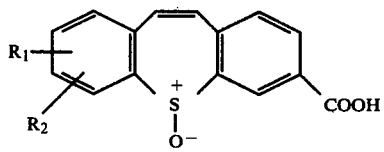

XIII

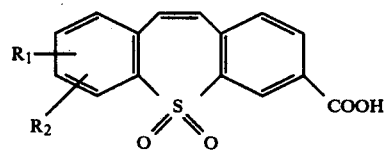

XIV

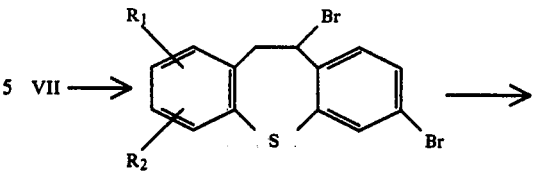

XV

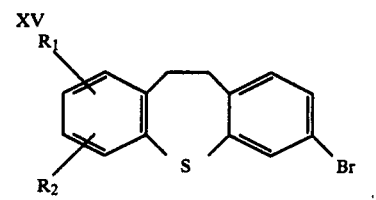

XVI

The bromine in XVI can be displaced by cuprous cyanide in a high-boiling polar solvent such as dimethylformamide, and the resulting 3-nitrile XVII hydrolyzed with aqueous mineral acid or base to give the 10,11-dihydrodibenzo[b,f]thiepin-3-carboxylic acid XVIII.

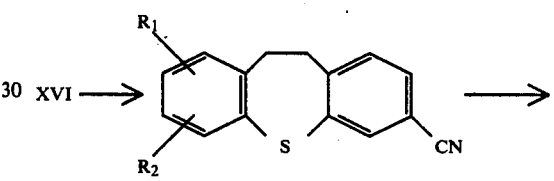

XVII

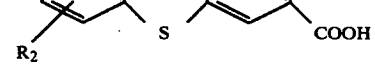

XVIII

Compounds of type I where the 10,11-double bond is saturated are prepared from intermediates VII, by displacement of the hydroxy using PBr₃, and reduction of the resulting 3,11-dibromide XV by NaBH₄ in a solvent such as sulfolane to yield the 3-bromo-10,11-dihydro derivative XVI.

Compound XVII can be oxidized with one equivalent of an organic peroxide, such as m-chloroperbenzoic acid, to yield the sulfoxide XIX which can then be hydrolyzed with mineral acid or base to the carboxylic acid XX. Compound XVII may also be oxidized with two equivalents of the oxidizing agent to afford the corresponding sulfone XXI, which on hydrolysis gives the acid XXII.

XVII —→ 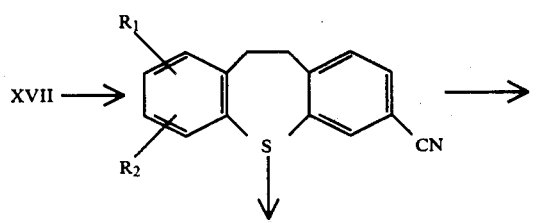

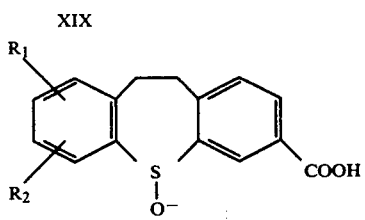
XX

XVII —→ 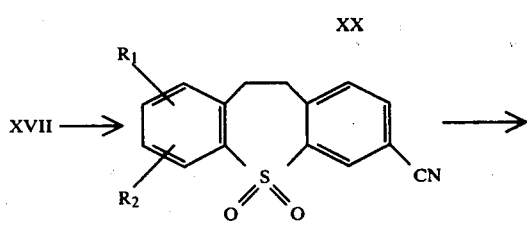

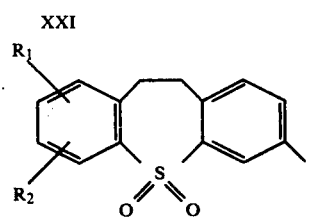
XXII

Substituent $R_1$ in I ($R_2$=H) can also be introduced by modification of the nitro group in IX or XVII ($R_1$=NO$_2$, $R_2$=H) by known procedures. For example, XXIII can be reduced with stannous chloride in acidic medium, hydrochloric acid, and the like, to yield XXIV which can be hydrolyzed with mineral acids or bases to XXV.

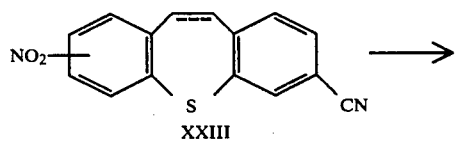
XXIII

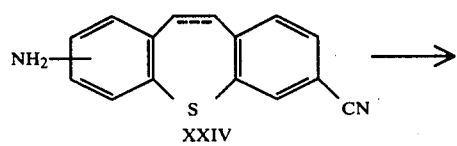
XXIV

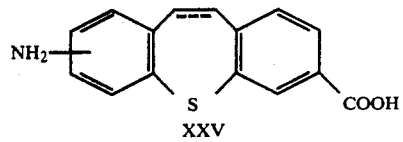
XXV

Alternatively, XXIII may be oxidized with peroxides, for example, m-chloroperbenzoic acid to yield XXVI which can be reduced to XXVII and then hydrolyzed with mineral acids or bases to XXVIII.

XXIII —→ 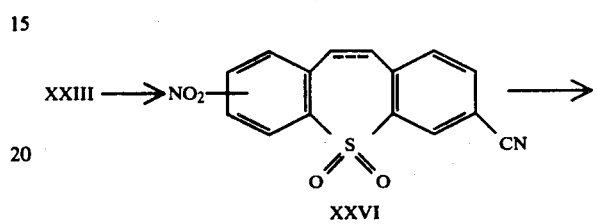

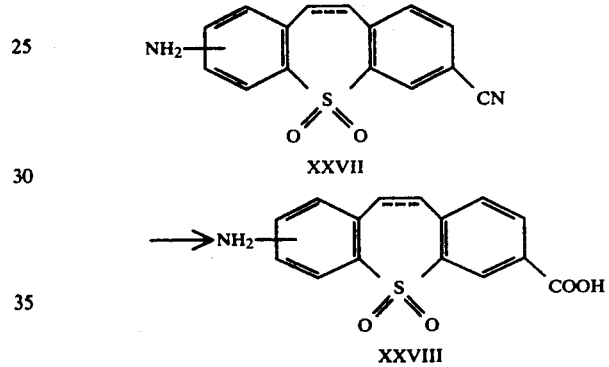

Intermediate XXIV can be reacted with sodium nitrite in mineral acid to the diazonium salt XXIX, where X is a mineral acid counter ion, for example, Cl$^{-1}$, HSO$_4^-$, BF$_4^-$, and the like, which on reaction with CuCl and CuCl$_2$ yields intermediate XXX which can be hydrolyzed to the acid XXXI. Intermediate XXX may also be oxidized to the sulfone derivative XXXII, then followed by a hydrolysis to the carboxylic acid XXXIII.

XXIV —→ 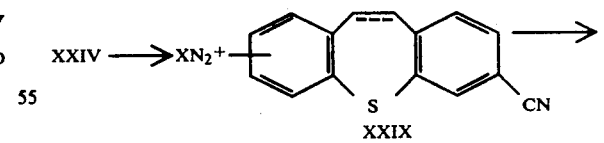

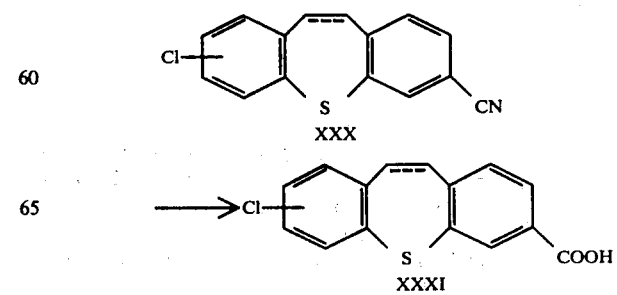

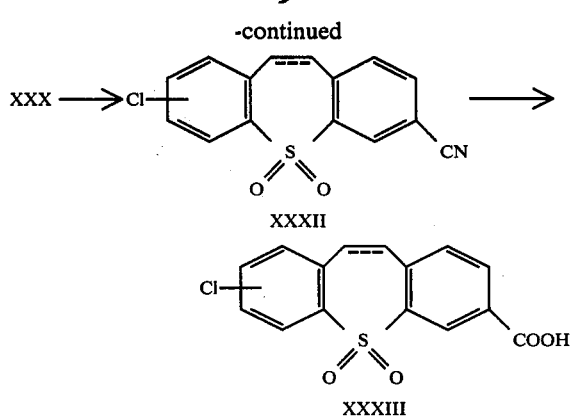
XXXII

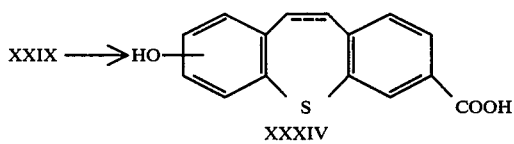
XXXIII

Derivative XXIX can be hydrolyzed with a solution of sulfuric acid 10 to 50% in strength at temperatures ranging from 0° to 90° C. to yield XXXIV. XXIX may also be reacted with potassium thioxanthate at temperatures from 40° to 70° C. followed by basic hydrolysis to yield the thiol acid XXXV.

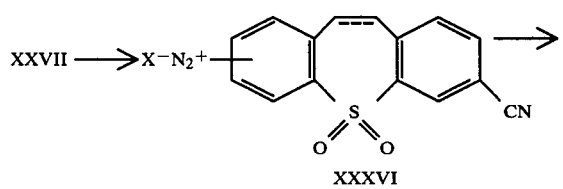
XXXIV

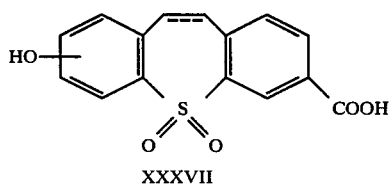
XXXV

Compound XXVII can be transformed in the usual manner to the diazonium salt XXXVI, which can be reacted as described above to yield compounds XXXVII and XXXVIII.

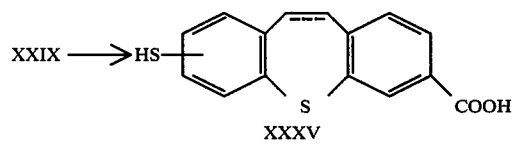
XXXVI

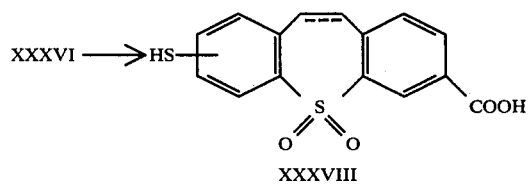
XXXVII

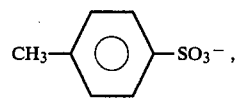
XXXVIII

Compounds XXXIV, XXXV, XXXVII, and XXXVIII can be reacted with alkyl halides RS in which R is a loweralkyl $C_1$ to $C_4$, benzyl, and X is a leaving group such as Cl, Br, I, and $$CH_3-\text{⟨C₆H₄⟩}-SO_3^-,$$

in the presence of bases such as alkali carbonate, hydroxides, and the like, in solvents such as dimethylformamide, at temperatures ranging from 30° to 160° C. to yield XXXIX, XL, XLI, and XLII, respectively.

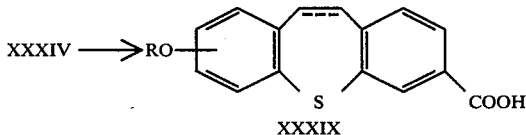
XXXIX

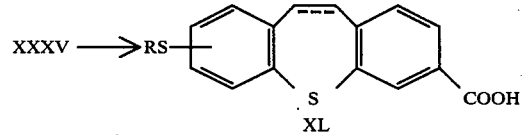
XL

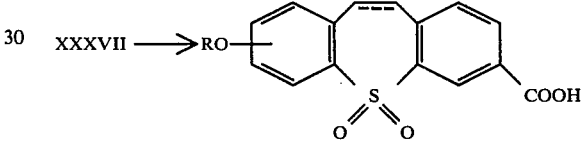
XLI

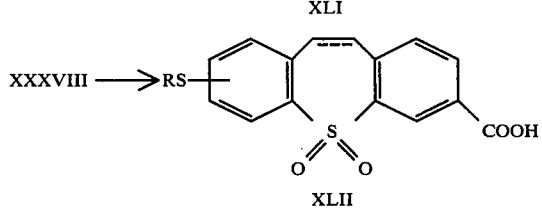
XLII

Compound XL can in a controlled oxidation with peroxides such as hydrogen peroxide or organic peroxy acids such as m-chloroperbenzoic acid, yield compound XLIII. XLII may be oxidized with one equivalent of organic peroxides such as m-chloroperbenzoic acid or with hydrogen peroxide in hydroxylic solvents such as alcohols, organic acids such as acetic acid, at temperatures below 30° C., to yield XLIV. Compounds XL, XLII, and XLIV may also be oxidized with excess organic peroxides such as m-chloroperbenzoic acid at room temperature, or with peroxides such as hydrogen peroxide in acidic medium such as acetic acid at temperatures between 80° and 100° C. to yield XLV.

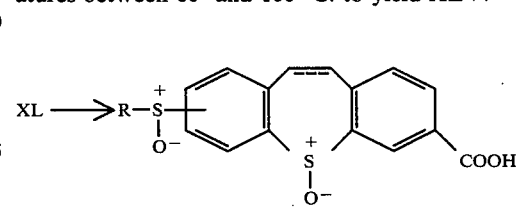
XLIII

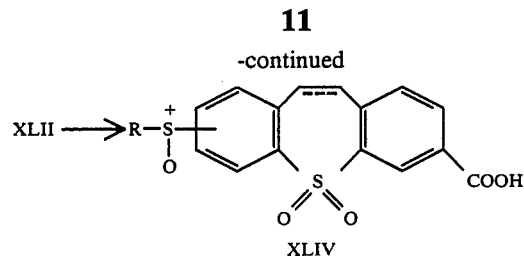

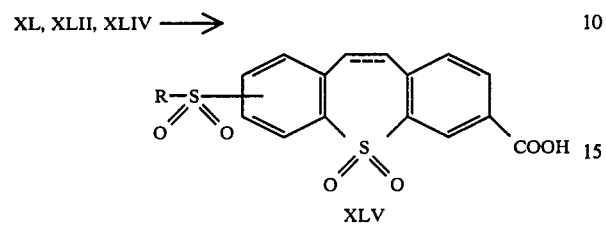

Specific introduction of substituents in position 8 in I can also be achieved as follows. For example, XVII ($R_1 = R_2 = H$) can react with alkanoyl halide RCOX or alkanoic anhydride RCOOCOR in which R is a loweralkyl $C_1$ to $C_4$ and X is chloro or bromo, under Freidel-Crafts conditions, to yield the 8-substituted acyl derivative XLVI; the 10,11-bridge may be brominated with a brominating agent such as N-bromosuccinimide, and treatment with a base such as DBN can generate the 10,11-unsaturated derivative XLVII.

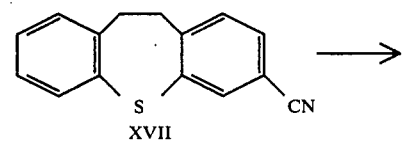

Both XLVI and XLVII can be hydrolyzed with mineral acid or base to the corresponding acids XLVIII and XLIX.

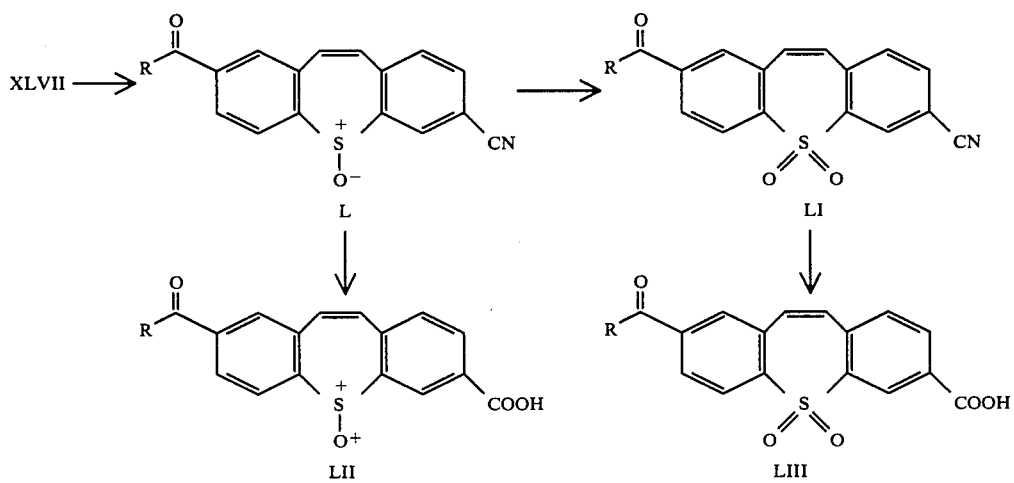

XLVII can be oxidized with oxidizing agents such as m-chloro perbenzoic acid stepwise to yield sulfoxide L and sulfone LI which are hydrolyzed under acidic or basic conditions to afford acids LII and LIII respectively.

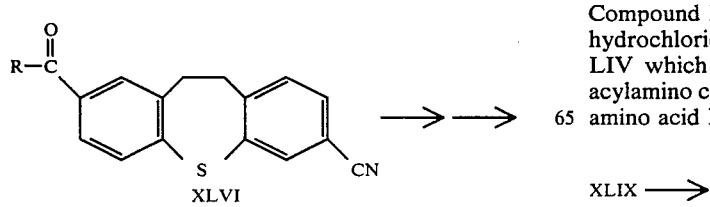

Compound XLIX can be reacted with hydroxylamide hydrochloride with presence of base to yield oxime LIV which on a Beckman rearrangement, yields the acylamino compound LV which upon hydrolysis yields amino acid LVI.

XLIX ⟶

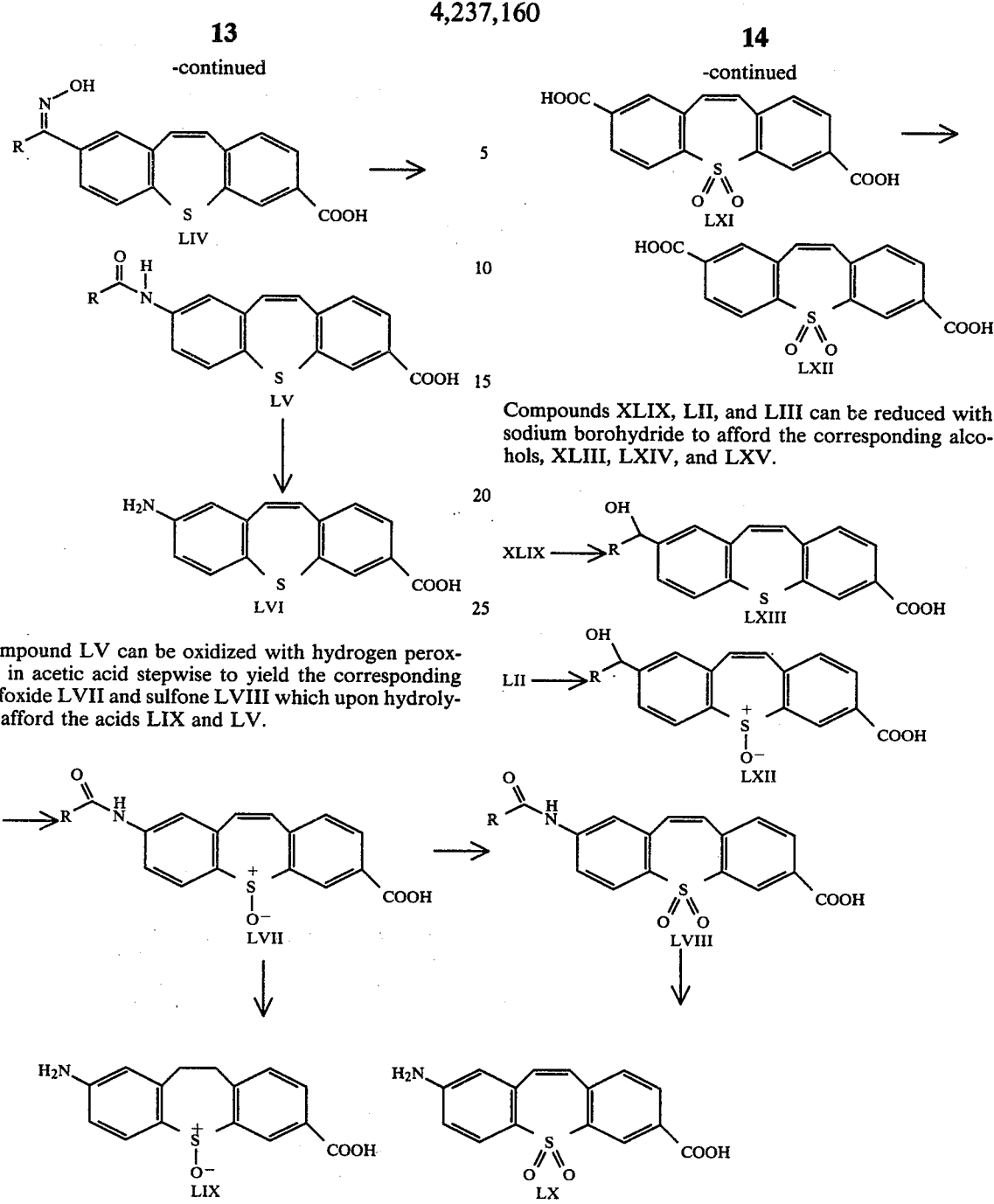

Compounds XLIX, LII, and LIII can be reduced with sodium borohydride to afford the corresponding alcohols, XLIII, LXIV, and LXV.

Compound LV can be oxidized with hydrogen peroxide in acetic acid stepwise to yield the corresponding sulfoxide LVII and sulfone LVIII which upon hydrolysis afford the acids LIX and LV.

Compounds LVI, LIX, and LX can be treated in various Sandmeyer reactions as described earlier to yield I substituted in the 8 position.

Compound XLIX (R=CH$_3$), when treated with sodium hypochlorite and base at temperatures from 0° to 70° C. for half an hour, yield the diacid LXI. When the process is carried for two days under the same conditions, LXII is obtained.

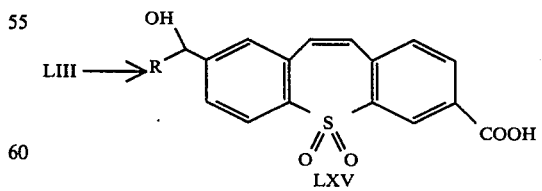

The higher homologs of Compound X hereinabove are prepared, starting with the appropriately substituted 3-carboxylic acid, through reduction, bromination, cyanization, and hydrolysis, to afford the corresponding 3-acetic acid derivative. Quite obviously, the described reduction, bromination, cyanization, and hydrolysis sequence can be repeated, employing the 3-acetic acid derivative as starting material, in order to obtain the corresponding propionic acid derivative which, in turn, can be employed as starting material for preparing the corresponding butyric acid derivative. In this manner, any desired 3-loweralkanoic acid derivative is readily prepared. Corresponding sulfinyl or sulfonyl derivatives are prepared by the oxidation techniques previously described.

EXAMPLE 1

3-Hydroxymethyl-10,11-dihydrodibenzo[b,f]thiepin

Dissolve 7.5 gm. of 10,11-dihydrodibenzo[b,f]-thiepin-3-carboxylic acid in 140 ml. of tetrahydrofuran. With stirring, add 90 ml. of 1 N diborane in tetrahydrofuran. Stir at room temperature for 2 hours and dilute the reaction mixture with water. Extract into ether, and evaporate the ether extract to dryness. Stir the residue with hexane and filter to obtain the title product (m.p., 82°–84° C.).

EXAMPLE 2

3-Hydroxymethyl-10,11-dihydrodibenzo[b,f]thiepin-5-oxide

Dissolve 2 gm. of 3-hydroxymethyl-10,11-dihydrodibenzo[b,f]thiepin in 200 ml. of methylene chloride at room temperature. Add 1.7 gm. of m-chloroperbenzoic acid. Stir at room temperature for 2 hours. Add 4 gm. of calcium hydroxide and 50 ml. of methylene chloride. Continue stirring for 15 minutes. Filter through celite and evaporate the filtrate to dryness. Crystallize the residue from toluene to obtain the title product (m.p., 144°–146° C.).

EXAMPLE 3

3-Hydroxymethyl-10,11-dihydrodibenzo[b,f]thiepin-5,5-dioxide

Repeat the process of Example 6, substituting an equivalent quantity of 10,11-dihydrodibenzo[b,f]thiepin-3-carboxylic acid-5,5-dioxide for the dibenzo[b,f]-thiepin-3-carboxylic acid-5,5-dioxide, to obtain the title product (m.p., 128°–130° C.).

EXAMPLE 4

3-Hydroxymethyldibenzo[b,f]thiepin

Repeat the process of Example 1, substituting an equivalent quantity of dibenzo[b,f]thiepin-3-carboxylic acid for the 10,11-dihydrodibenzo[b,f]thiepin-3-carboxylic acid, to obtain the title product (m.p., 111°–112° C.).

EXAMPLE 5

3-Hydroxymethyldibenzo[b,f]thiepin-5-oxide

Repeat the process of Example 2, substituting an equivalent quantity of 3-hydroxymethyldibenzo[b,f]-thiepin for the 3-hydroxymethyl-10,11-dihydrodibenzo[b,f]thiepin, to obtain the title product (m.p., 146°–148° C.).

EXAMPLE 6

3-Hydroxymethyldibenzo[b,f]thiepin-5,5-dioxide

Mix 2.8 gm. of dibenzo[b,f]thiepin-3-carboxylic acid-5,5-dioxide, 50 ml. of tetrahydrofuran, and 30 ml. of 1 N diborane in tetrahydrofuran. Stir at room temperature for 1 hour. Dilute the reaction mixture with water, and extract into ether. Evaporate the ether extract to dryness. Stir the residue in ether, and filter to obtain the title product (m.p., 156°–158° C.).

EXAMPLE 7

3-Hydroxymethyl-8-nitro, dibenzo[b,f]thiepin

Repeat the process of Example 1, substituting an equivalent quantity of 8-nitrodibenzo[b,f]thiepin-3-carboxylic acid for the 10,11-dihydrodibenzo[b,f]thiepin-3-carboxylic acid, to obtain the title product.

EXAMPLE 8

3-Hydroxymethyl-8-nitro-dibenzo[b,f]thiepin-5-oxide

Repeat the process of Example 2, substituting an equivalent quantity of 3-hydroxymethyl-8-nitro-dibenzo[b,f]thiepin for the 3-hydroxymethyl-10,11-dihydrodibenzo[b,f]thiepin, to obtain the title product.

EXAMPLE 9

3-Hydroxymethyl-8-nitro-dibenzo[b,f]thiepin-5,5-dioxide

Repeat the process of Example 6, substituting an equivalent quantity of 8-nitrodibenzo[b,f]thiepin-3-carboxylic acid 5,5-dioxide for the dibenzo[b,f]thiepin-3-carboxylic acid 5,5-dioxide, to obtain the title product.

EXAMPLE 10

8-Amino-3-hydroxymethyl-dibenzo[b,f]thiepin

Repeat the process of Example 1, substituting an equivalent quantity of 8-aminodibenzo[b,f]thiepin-3-carboxylic acid for the 10,11-dihydrodibenzo[b,f]thiepin-3-carboxylic acid, to obtain the title product.

EXAMPLE 11

8-Amino-3-hydroxymethyl-dibenzo[b,f]thiepin 5,5-dioxide

Repeat the process of Example 6, substituting an equivalent quantity of 8-amino-dibenzo[b,f]thiepin-3-carboxylic acid 5,5-dioxide for the dibenzo[b,f]thiepin-3-carboxylic acid 5,5-dioxide, to obtain the title product.

EXAMPLE 12

8-Chloro-3-hydroxymethyl-dibenzo[b,f]thiepin

Repeat the process of Example 1, substituting an equivalent quantity of 8-chlorodibenzo[b,f]thiepin-3-carboxylic acid for the 10,11-dihydro-dibenzo[b,f]thiepin-3-carboxylic acid, to obtain the title product.

EXAMPLE 13

8-Chloro-3-hydroxymethyl-dibenzo[b,f]thiepin 5,5-dioxide

Repeat the process of Example 6, substituting an equivalent quantity of 8-chloro-dibenzo[b,f]thiepin-3-carboxylic acid 5,5-dioxide for the dibenzo[b,f]thiepin-3-carboxylic acid 5,5-dioxide, to obtain the title product.

EXAMPLE 14

8-Hydroxy-3-hydroxymethyl-dibenzo[b,f]thiepin

Repeat the process of Example 1, substituting an equivalent quantity of 8-hydroxy-dibenzo[b,f]thiepin-3-carboxylic acid for the 10,11-dihydro-dibenzo[b,f]thiepin-3-carboxylic acid, to obtain the title product.

EXAMPLE 15

8-Hydroxy-3-hydroxymethyl-dibenzo[b,f]thiepin-5,5-dioxide

Repeat the process of Example 6, substituting an equivalent quantity of 8-hydroxy-dibenzo[b,f]thiepin-3-carboxylic acid 5,5-dioxide for the dibenzo[b,f]thiepin-3-carboxylic acid 5,5-dioxide, to obtain the title product.

EXAMPLE 16

3-Hydroxymethyl-8-mercapto-dibenzo[b,f]thiepin

Repeat the process of Example 1, substituting an equivalent quantity of 8-mercaptodibenzo[b,f]thiepin-3-carboxylic acid for the 10,11-dihydro-dibenzo[b,f]thiepin-3-carboxylic acid, to obtain the title product.

EXAMPLE 17

3-Hydroxymethyl-8-mercapto-10,11-dihydrodibenzo[b,f]thiepin-5,5-dioxide

Repeat the process of Example 6, substituting an equivalent quantity of 8-mercapto-10,11-dihydrodibenzo[b,f]thiepin-3-carboxylic acid 5,5-dioxide for the dibenzo[b,f]thiepin-3-carboxylic acid 5,5-dioxide, to obtain the title product.

EXAMPLE 18

3-Hydroxymethyl-8-methoxy-dibenzo[b,f]thiepin

Repeat the process of Example 1, substituting an equivalent quantity of 8-methoxy-dibenzo[b,f]thiepin-3-carboxylic acid for the 10,11-dihydrodibenzo[b,f]thiepin-3-carboxylic acid, to obtain the title product.

EXAMPLE 19

3-Hydroxymethyl-8-methoxy-dibenzo[b,f]thiepin-5,5-dioxide

Repeat the process of Example 6, substituting an equivalent quantity of 8-methoxy-dibenzo[b,f]thiepin-3-carboxylic acid 5,5-dioxide for the dibenzo[b,f]thiepin3-carboxylic acid 5,5-dioxide, to obtain the title product.

EXAMPLE 20

3-Hydroxymethyl-8-methylthio-dibenzo[b,f]thiepin

Repeat the process of Example 1, substituting an equivalent quantity of 8-methylthiodibenzo[b,f]thiepin-3-carboxylic acid for the 10,11-dihydrodibenzo[b,f]thiepin-3-carboxylic acid, to obtain the title product.

EXAMPLE 21

3-Hydroxymethyl-8-methylthio-dibenzo[b,f]thiepin-5,5-dioxide

Repeat the process of Example 6, substituting an equivalent quantity of 8-methylthiodibenzo[b,f]thiepin-3-carboxylic acid 5,5-dioxide for the dibenzo[b,f]thiepin-3-carboxylic acid 5,5-dioxide, to obtain the title product.

EXAMPLE 22

3-Hydroxymethyl-8-methylsulfinyl-dibenzo[b,f]thiepin-5,5-dioxide

Repeat the process of Example 6, substituting an equivalent quantity of 8-methylsulfinyldibenzo[b,f]thiepin-3-carboxylic acid 5,5-dioxide for the dibenzo[b,f]thiepin-3-carboxylic acid 5,5-dioxide, to obtain the title product.

EXAMPLE 23

3-Hydroxymethyl-8-methylsulfinyl-dibenzo[b,f]thiepin-5-oxide

Repeat the process of Example 2, substituting an equivalent quantity of 3-hydroxymethyl-8-methylthiodibenzo[b,f]thiepin for the 3-hydroxymethyl-dibenzo[b,f]thiepin, to obtain the title product.

EXAMPLE 24

3-Hydroxymethyl-8-methylsulfonyl-dibenzo[b,f]thiepin-5,5-dioxide

Repeat the process of Example 6, substituting an equivalent quantity of 8-methylsulfonyldibenzo[b,f]thiepin-3-carboxylic acid 5,5-dioxide for the dibenzo[b,f]thiepin-3-carboxylic acid 5,5-dioxide, to obtain the title product.

EXAMPLE 25

8-Acetyl-3-hydroxymethyl-10,11-dihydrodibenzo[b,f]thiepin

Repeat the process of Example 1, substituting an equivalent quantity of 8-acetyl-10,11-dihydrodibenzo[b,f]thiepin-3-carboxylic acid for the 10,11-dihydrodibenzo[b,f]thiepin-3-carboxylic acid, to obtain the title product.

EXAMPLE 26

8-Acetyl-3-hydroxymethyl-10,11-dihydrodibenzo[b,f]thiepin 5,5-dioxide

Repeat the process of Example 6, substituting an equivalent quantity of 8-acetyl-10,11-dihydrodibenzo[b,f]thiepin-3-carboxylic acid 5,5-dioxide for the dibenzo[b,f]thiepin-3-carboxylic acid 5,5-dioxide, to obtain the title product.

EXAMPLE 27

3,8-Dihydroxymethyl-10,11-dihydrodibenzo[b,f]thiepin

Repeat the process of Example 1, substituting an equivalent quantity of 8-hydroxymethyl-10,11-dihydrodibenzo[b,f]thiepin-3-carboxylic acid for the 10,11-dihydrodibenzo[b,f]thiepin-3-carboxylic acid, to obtain the title product.

EXAMPLE 28

3,8-Dihydroxymethyl-10,11-dihydrodibenzo[b,f]thiepin 5,5-dioxide

Repeat the process of Example 6, substituting an equivalent quantity of 8-hydroxymethyl-10,11-dihydrodibenzo[b,f]thiepin-3-carboxylic acid 5,5-dioxide for the dibenzo[b,f]thiepin-3-carboxylic acid 5,5-dioxide, to obtain the title product.

EXAMPLE 29

3(2-Hydroxyethyl)-11-oxo-10,11-dihydrodibenzo[b,f]thiepin 5,5-dioxide

Repeat the process of Example 6, substituting an equivalent quantity of 10,11-dihydro-11-oxodibenzo[b,f]thiepin-3-acetic acid 5,5-dioxide for the dibenzo[b,f]thiepin-3-carboxylic acid, to obtain the title product.

EXAMPLE 30

8-Fluoro-3-hydroxymethyl-10,11-dihydrodibenzo[b,f]-thiepin

Repeat the process of Example 1, substituting an equivalent quantity of 8-fluoro-10,11-dihydrodibenzo[b,f]thiepin-3-carboxylic acid for the 10,11-dihydrodibenzo[b,f]thiepin-3-carboxylic acid, to obtain the title product (m.p., 80°–81° C.).

EXAMPLE 31

8-Fluoro-3-hydroxymethyl-10,11-dihydrodibenzo[b,f]-thiepin 5-oxide

Repeat the process of Example 2, substituting an equivalent quantity of 8-fluoro-3-hydroxymethyl-10,11-dihydrodibenzo[b,f]thiepin for the 3-hydroxymethyldibenzo[b,f]thiepin, to obtain the title product (m.p. 181°–183° C.).

EXAMPLE 32

8-Fluoro-3-hydroxymethyl-10,11-dihydrodibenzo[b,f]-thiepin 5,5-dioxide

Repeat the process of Example 6, substituting an equivalent quantity of 8-fluoro-10,11-dihydrodibenzo[b,f]thiepin-3-carboxylic acid 5,5-dioxide for the dibenzo[b,f]thiepin-3-carboxylic acid 5,5-dioxide, to obtain the title product (m.p., 116°–118° C.).

EXAMPLE 33

8-Fluoro-3-hydroxymethyl-dibenzo[b,f]thiepin

Repeat the process of Example 1, substituting an equivalent quantity of 8-fluorodibenzo[b,f]thiepin-3-carboxylic acid for the 10,11-dihydrodibenzo[b,f]thiepin-3-carboxylic acid, to obtain the title product (m.p., 123°–125° C.).

EXAMPLE 34

8-Fluoro-3-hydroxymethyl-dibenzo[b,f]thiepin-5-oxide

Repeat the process of Example 2, substituting an equivalent quantity of 8-fluoro-3-hydroxymethyldibenzo[b,f]thiepin for the 3-hydroxymethyldibenzo[b,f]thiepin to obtain the title product (m.p., 161°–163° C.).

EXAMPLE 35

8-Fluoro-3-hydroxymethyl-dibenzo[b,f]thiepin-5,5-dioxide

Repeat the process of Example 6, substituting an equivalent quantity of 8-fluorodibenzo[b,f]thiepin-3-carboxylic acid 5,5-dioxide for the dibenzo[b,f]thiepin-3-carboxylic acid 5,5-dioxide, to obtain the title product (m.p., 131°–133° C.).

The compounds of formula I wherein Z is defined as sulfinyl are capable of existing as optical isomers because of the tetrahedral structure of the sulfoxide substituent. Thus, the sulfoxide disclosed in the Examples are racemic mixtures of D and L isomers which may be resolved by known procedures into their enantiomers. Each of the enantiomorphic isomers may exhibit variation in biological potency. Thus, the compounds of Examples 2, 5, 8, 11, 23, 32, and 35, may be resolved by conventional procedures into their D and L enantiomorphs.

The compounds of formula I are useful in the treatment or prophylaxis of mammalian disease conditions where excessive undesirable contractile activity of prostaglandins, such as $PGF_{2\alpha}$, or prostaglandin biosynthetic intermediates contribute. These conditions include asthma, inflammatory states such as arthritis, allergy, diarrhea, hypertension, angina, platelet aggregation, cerebral spasm, premature abortion, and dismenorrhea. In particular, they are of value in reaginic mediated asthma (extrinsic asthma).

The magnitude of a prophylactic or therapeutic dose of compound of formula I will, of course, vary with the nature and the severity of the condition to be treated and with the particular compound of formula I and its route of administration. In general, the dose range lies within the range of 0.2 mg. to 100 mg. per kg. body weight of a mammal.

The pharmaceutical compositions of the present invention comprise a compound of formula I as an active ingredient, and may also contain pharmaceutically acceptable carrier and optionally other therapeutic ingredients. The compositions include compositions suitable for oral, rectal, opthalmic, pulmonary, nasal, dermal, topical, or parenteral (including subcutaneous, intramuscular, and intravenous) administration, although the most suitable route in any given case will depend on the nature and severity of the condition being treated and on the nature of the active ingredient. They may be conveniently presented in unit dosage form and prepared by any of the methods well known in the art of pharmacy.

For use where a composition for intravenous administration is employed, a suitable dosage range is from 0.2 to 10 mg. (preferably 1 to 5 mg.) of a compound of formula I per kg. of body weight per day, and in the case where an oral composition is employed a suitable dosage range is about, e.g., 1 to 50 mg. of a compound of formula I per kg. of body weight per day, preferably from 10 to 40 mg./kg.

Pharmaceutical compositions of the present invention suitable for oral administration and by inhalation in the case of asthma therapy may be presented as discrete units such as capsules, cachets, or tablets each containing a predetermined amount of the active ingredient; as a powder or granules; or as a solution or a suspension in an aqueous liquid, a non-aqueous liquid, an oil-in-water emulsion, or a water-in-oil liquid emulsion. Such compositions may be prepared by any of the methods of pharmacy but all methods include the step of bringing into association the active ingredient with the carrier which constitutes one or more necessary ingredients. In general, the compositions are prepared by uniformly and intimately admixing the active ingredient with liquid carriers or finely divided solid carriers or both, and then, if necessary, shaping the product into the desired presentation. For example, a tablet may be prepared by compression or moulding, optionally with one or more accessory ingredients. Compressed tablets may be prepared by compressing in a suitable machine, the active ingredient in a free-flowing form such as powder or granules, optionally mixed with a binder, lubricant, inert diluent, lubricating, surface active or dispersing agent. Moulded tablets may be made by moulding in a suitable machine, a mixture of the powdered compound moistened with an inert liquid diluent. Desirably, each tablet contains from 50 mg. to 500 mg. of the active ingredient and each cachet or capsule contains from 50 mg. to 500 mg. of the active ingredient.

Although the instant invention has been described in the foregoing specification in terms of the use of the novel thiepin disclosed herein in the treatment and control of human and warm-blooded animal disease conditions characterized by excessive undesirable contractile activity of prostaglandins and prostaglandin biosynthetic intermediates, and particularly of asthma, it will be recognized by those skilled in the art that, in addition to the involvement of contractile prostaglandins in chronic obstructive lung disease (e.g., asthma), prostaglandins play a role in other allergic conditions as well as in inflammation, diarrhea, hypertension, angina, cerebral spasm, premature abortion, and dysmenorrhea. Also, the thiepins of this invention are potent $TXA_2$ biosynthesis inhibitors, inhibiting platelet aggregation, and can be useful in diseases such as atherosclerosis, varient anginal and myocardial infarction. Applicants consider application of the thiepins disclosed and claimed herein to the treatment and control of such disease conditions to be obvious equivalents to the invention as disclosed by Applicants and to fall within the scope of the instant invention.

The subject matter which Applicants regard as their invention, and which is sought to be patented herein, is particularly pointed and distinctly claimed as follows.

What is claimed is:

1. A compound of the formula:

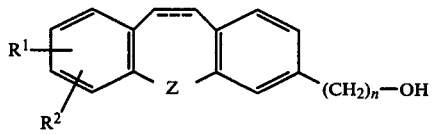

or an ester or acetal thereof, wherein n is an integer from 1 to 4;

Z is thio, sulfinyl, or sulfonyl;

$R^1$ and/or $R^2$ is hydrogen, halogen including chloro, bromo, fluoro and iodo, amino, $C_1$ to $C_4$ alkyl, $C_1$ to $C_4$ alkanoyl, hydroxyl, $C_1$ to $C_4$ alkoxy, thiol, $C_1$ to $C_4$ alkylthio, $C_1$ to $C_4$ alkylsulfinyl, $C_1$ to $C_4$ alkylsulfonyl, trifluoromethyl, trifluoromethylthio, cyano, nitro, and $C_1$ to $C_4$ alkyl or dialkylamino, aralkyl including benzyl and phenethyl, hydroxyalkyl as $CH_3CHOH$; and the dotted line indicates either an olefinic bond or saturation at the 10-, 11-position.

2. A compound according to claim 1 where Z is thio.

3. A compound according to claim 1 where the dotted line indicates an olefinic bond.

4. A compound according to claim 1 where the dotted line indicates saturation.

5. A compound according to claim 3, 3-hydroxymethyldibenzo[b,f]thiepin.

6. A compound according to claim 3, 3-hydroxymethyldibenzo[b,f]thiepin-5-oxide.

7. A compound according to claim 3, which is 3-hydroxymethyldibenzo[b,f]thiepin-5,5-dioxide.

8. A compound according to claim 3, which is 8-fluoro-3-hydroxymethyl-dibenzo[b,f]thiepin.

9. A compound according to claim 2, which is 8-fluoro-3-hydroxymethyl-dibenzo[b,f]thiepin-5-oxide.

10. A compound according to claim 3, which is 8-fluoro-3-hydroxymethyl-dibenzo[b,f]thiepin-5,5-dioxide.

11. A compound according to claim 4, which is 3-hydroxymethyl-10,11-dihydrodibenzo[b,f]thiepin.

12. A compound according to claim 4, which is 3-hydroxymethyl-10,11-dihydrodibenzo[b,f]thiepin-5-oxide.

13. A compound according to claim 4, which is 3-hydroxymethyl-10,11-dihydrodibenzo[b,f]thiepin-5,5-dioxide.

14. A compound according to claim 4, which is 8-fluoro-3-hydroxymethyl-10,11-dihydrodibenzo[b,f]thiepin.

15. A compound according to claim 4, which is 8-fluoro-3-hydroxymethyl-10,11-dihydrodibenzo[b,f]thiepin 5-oxide.

16. A compound according to claim 4, which is 8-fluoro-3-hydroxymethyl-10,11-dihydrodibenzo[b,f]thiepin-5,5-dioxide.

17. A composition for treating undesirable contractile activity of prostaglandins consisting essentially of a pharmaceutically acceptable carrier and a therapeutically effective amount of a compound of the formula:

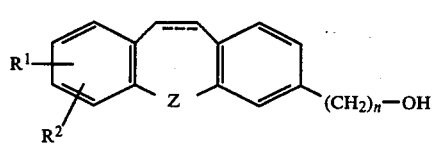

or an ester or acetal thereof, wherein n is an integer from 1 to 4;

Z is thio, sulfinyl, or sulfonyl;

$R^1$ and/or $R^2$ is hydrogen, halogen including chloro, bromo, fluoro and iodo, amino, $C_1$ to $C_4$ alkyl, $C_1$ to $C_4$ alkanoyl, hydroxyl, $C_1$ to $C_4$ alkoxy, thiol, $C_1$ to $C_4$ alkylthio, $C_1$ to $C_4$ alkylsulfinyl, $C_1$ to $C_4$ alkylsulfonyl, trifluoromethyl, trifluoromethylthio, cyano, nitro, and $C_1$ to $C_4$ alkyl or dialkylamino, aralkyl including benzyl and phenethyl, hydroxyalkyl as $CH_3CHOH$; and the dotted line indicates either an olefinic bond or saturation at the 10-, 11-position.

18. A process for preparing a compound of the formula:

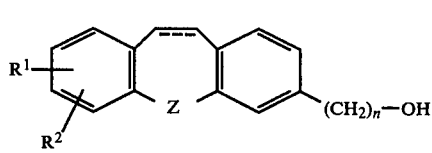

or an ester or acetal thereof, wherein n is an integer from 1 to 4;

Z is thio, sulfinyl, or sulfonyl;

$R^1$ and/or $R^2$ is hydrogen, halogen including chloro, bromo, fluoro and iodo, amino, $C_1$ to $C_4$ alkyl, $C_1$ to $C_4$ alkanoyl, hydroxyl, $C_1$ to $C_4$ alkoxy, thiol, $C_1$ to $C_4$ alkylthio, $C_1$ to $C_4$ alkylsulfinyl, $C_1$ to $C_4$ alkylsulfonyl, trifluoromethyl, trifluoromethylthio, cyano, nitro, and $C_1$ to $C_4$ alkyl or dialkylamino, aralkyl including benzyl and phenethyl, hydroxyalkyl as $CH_3CHOH$; and the dotted line indicates either an olefinic bond or saturation at the 10-, 11-position;

which comprises reducing a compound of the formula:

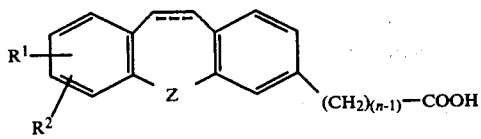

with an alkali metal aluminum hydride or borane to convert the COOH substituent into a hydroxymethyl substituent.

19. The compound according to claim 1 wherein $R^1$ is hydrogen and $R^2$ is fluoro.

20. The compound according to claim 1 wherein $R^1$ is hydrogen and $R^2$ is amino.

21. The compound according to claim 1 wherein $R^1$ is hydrogen and $R^2$ is chloro.

22. The compound according to claim 1 wherein $R^1$ is hydrogen and $R^2$ is acetyl.

* * * * *